United States Patent [19]

Naitou et al.

[11] Patent Number: 4,650,652

[45] Date of Patent: Mar. 17, 1987

[54] PROCESS FOR RECOVERING HIGHLY PURE RARE EARTH OXIDES FROM A WASTE RARE EARTH PHOSPHOR

[75] Inventors: Masaru Naitou, Isehara; Masatake Yoshikawa, Hiratsuka; Kinichiro Narita, Chigasaki, all of Japan

[73] Assignee: Kasei Optonix, Ltd., Tokyo, Japan

[21] Appl. No.: 694,282

[22] Filed: Jan. 24, 1985

[30] Foreign Application Priority Data

Jan. 31, 1984 [JP] Japan .................................. 59-14441

[51] Int. Cl.$^4$ .............................................. C01F 17/00
[52] U.S. Cl. ...................................... 423/21.1; 423/263
[58] Field of Search ........................................ 423/21.1

[56] References Cited

U.S. PATENT DOCUMENTS

| | | | |
|---|---|---|---|
| 3,506,585 | 4/1970 | Otsuka et al. | 423/21.1 |
| 4,198,231 | 4/1980 | Gusset | 423/21.1 |
| 4,400,360 | 8/1983 | Nalewajek | 423/21.1 |
| 4,405,568 | 9/1982 | Nalewajek | 423/21.1 |
| 4,438,078 | 3/1984 | Nalewajek | 423/21.1 |

FOREIGN PATENT DOCUMENTS

| | | | |
|---|---|---|---|
| 866715 | 4/1961 | United Kingdom | 423/21.1 |
| 1123583 | 12/1969 | United Kingdom | 423/21.1 |

Primary Examiner—H. I. Carter
Attorney, Agent, or Firm—Oblon, Fisher, Spivak, McClelland & Maier

[57] ABSTRACT

A process for recovering highly pure rare earth oxides from a waste rare earth phosphor containing at least Fe and/or Ca as impurities, which comprises dissolving the waste rare earth phosphor in an excess amount of a strong acid capable of dissolving the waste rare earth phosphor, adding to the solution at a temperature of at least 70° C. oxalic acid in an amount of from 0.3 to 1.8 times the theoretical amount to obtain precipitates of rare earth oxalates, washing the precipitates with warm water having a temperature of at least 50° C. and then baking them.

10 Claims, 1 Drawing Figure

PROCESS FOR RECOVERING HIGHLY PURE RARE EARTH OXIDES FROM A WASTE RARE EARTH PHOSPHOR

BACKGROUND OF THE INVENTION

1. Field of the Invention

The present invention relates to a process for recovering rare earth oxides from a waste rare earth phosphor.

2. Description of Prior Art

As red-emitting phosphors for CPT (Color Picture Tube) or CDT (Color Display Tube), rare earth phosphors such as $Y_2O_2S:Eu$, are widely employed. These phosphors contain expensive rare earth elements such as Y, Eu, Sm and Tb, as main components. Accordingly, they are comparatively expensive relative to the usual sulfide phosphors such as a blue-emitting phosphor ZnS:Ag or a green-emitting phosphor ZnS:Cu,Au,Al. During the preparation of these phosphors, it may happen that inferior products which do not meet the standard requirements are produced, or during the repeated use of such phosphors by mixing them with binders to form coating solutions for the production of cathode ray tubes, it may happen that impurities or foreign matters will be included to give inferior products. Heretofore, such rare earth phosphors failing to meet the standard requirements or phosphor coating solutions containing such inferior products (hereinafter referred to generally as "waste rare earth phosphors") used to be wasted. Namely, when the above-mentioned rare earth phosphors are employed for CPT or CDT, it is common to incorporate a very small amount of iron oxide (red iron oxide) as a red-pigment to improve the image quality, and it is common to use them together with a sulfide phosphor such as ZnS:Ag. Accordingly, waste rare earth phosphors not only are contaminated with impurities such as Fe, Zn, Ca or Al but also usually contain foreign matters such as metal fragments, inorganic pigments or organic substances. Up to the present there has been no economically feasible process for the recovery and purification of rare earth components from the waste rare earth phosphors.

As mentioned above, rare earth phosphors are expensive, and from the viewpoints of conservation of resources and economy, it is extremely advantageous to recover and reuse them as highly pure rare earth materials.

SUMMARY OF THE INVENTION

In view of the above-mentioned state of the art, it is an object of the present invention to recover rare earth components in high purity from a waste rare earth phosphor by an economically advantageous i.e. simple process.

According to the present invention, the above object can be accomplished by a process for recovering highly pure rare earth oxides from a waste rare earth phosphor containing at least Fe and/or Ca as impurities, which comprises dissolving the waste rare earth phosphor in an excess amount of a strong acid capable of dissolving the waste rare earth phosphor, adding to the solution at a temperature of at least 70° C. oxalic acid in an amount of from 0.3 to 1.8 times the theoretical amount to obtain precipitates of rare earth oxalates, washing the precipitates with warm water having a temperature of at least 50° C. and then baking them.

BRIEF DESCRIPTION OF THE DRAWING

In the accompanying drawing.

DETAILED DESCRIPTION OF THE INVENTION

Figure 1:
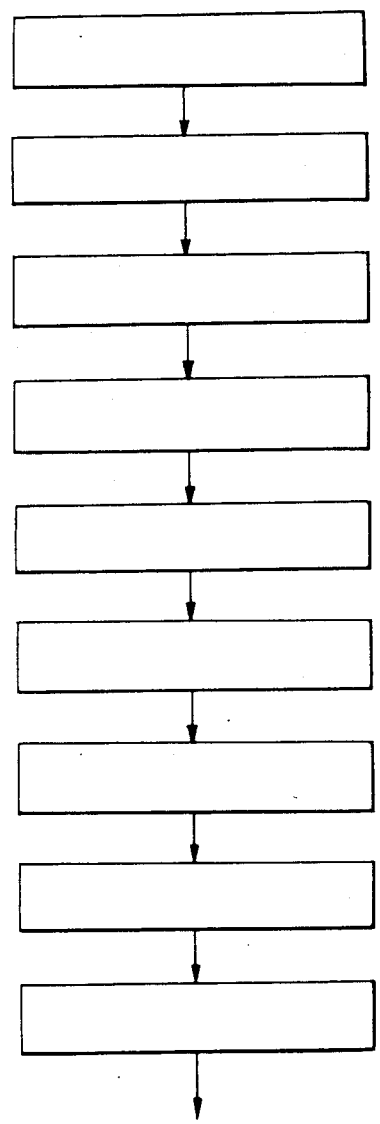
FIG. 1 shows process steps of a process according to the present invention.

Representative waste rare earth phosphors to which the process of the present invention may be applied, have compositions as identified in Table 1.

TABLE 1

| | TOTAL-RE (wt. %) | Fe (ppm) | Ca (ppm) | Zn (ppm) | Al (ppm) | Note |
|---|---|---|---|---|---|---|
| Sample 1 | 90.0 | 2000 | 150 | 2000 | | |
| Sample 2 | 94.7 | 1500 | 150 | 10000 | 4000 | |
| Sample 3 | 96.3 | 500 | 50.0 | 10000 | | |
| Sample 4 | 94.7 | 3000 | 10.0 | 2000 | | Contains substantial amounts of foreign matters |
| Sample 5 | 80.0 | 2000 | 200 | 10000 | | |

In the above Table, "TOTAL-RE" means a total amount of all rare earth compounds including elements such as Y, Eu, Tb, Sm and the like, as calculated as $RE_2O_2S$, for example $Y_2O_2S$. The reason why the total amount does not reach 100% is that foreign matters such as sand, waste fragments, iron rust, metal fragments, aluminum foil pieces or organic substances are contained. As is apparent from the compositions shown in Table 1, the typical waste rare earth phosphors to which the process of the present invention may be applied, have a total rare earth compound content "TOTAL-RE" of at least 80% by weight, a Fe content of at least 500 ppm and a Ca content of at least 10.0 ppm. These waste rare earth phosphors can be treated in accordance with the sequential process steps shown in FIG. 1.

For instance, in the first step of "weighing", the waste rare earth phosphor is first analyzed to ascertain the composition as shown in Table 1, and then there will be prepared pure water in an amount of from 7.0 to 8.0 times the weight of the sample powder, hydrochloric acid (HCl) in an amount of from 1.2 to 1.7 times, preferably 1.5 times the theoretically required amount of 6 mol of HCl as represented by the following reaction formula and hydrogen peroxide ($H_2O_2$) in an amount of from 2 to 7 times, preferably 5 times, the theoretically required amount of 1 mol of $H_2O_2$.

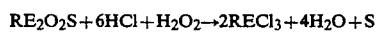

$$RE_2O_2S + 6HCl + H_2O_2 \rightarrow 2RECl_3 + 4H_2O + S$$

In the next step of "dissolving", pure water and hydrochloric acid are firstly added. Then, hydrogen peroxide is added. Inversely, after the addition of pure water, hydrogen peroxide may firstly be added, followed by the addition of hydrochloric acid. Otherwise, after the addition of pure water, hydrochloric acid and hydrogen peroxide may alternately be added in small portions. This step is particularly important to completely dissolve the waste rare earth phosphor especially when the waste rare earth phosphor is an oxysulfide. Further, in this dissolving step, the reaction solution may be heated to facilitate the reaction.

Other than the above-mentioned manner of dissolving by means of hydrochloric acid and hydrogen peroxide, the dissolving step may be conducted by means of a strong acid, such as nitric acid, which is capable of dissolving the waste rare earth phosphor.

For instance, in the case of nitric acid, the following reaction may be utilized.

$$RE_2O_2S + 8HNO_3 \rightarrow 2RE(NO_3)_3 + 4H_2O + S + 2NO_2$$

In this case, nitric acid is preferably added in an amount of from 1.5 to 3.0 times the theoretical amount represented by the reaction formula.

Further, for the dissolving step, there may be employed a mixture of two or more acids, e.g. a combination of hydrochloric acid and nitric acid.

As is evident from the foregoing, it is a feature of the present invention to add the strong acid capable of dissolving the waste rare earth phosphor in an amount in excess of the theoretical amount determined by the reaction formula.

Then, upon the completion of the reaction, the reaction solution is cooled and then subjected to filtration under reduced pressure by means of e.g. a Nutsche funnel to remove the insoluble components.

In the next second weighing step, pure water is dropwise added to the clear solution thus obtained (i.e. the filtrate) to bring the concentration of the rare earth ions to a level of $0.5 \pm 0.1$ g·ion per liter. This concentration is particularly important in that it is desirable to adjust the above-mentioned solution to a concentration within this range in order to obtain rare earth oxides having a Fe content of not higher than 5 ppm and a Ca content of not higher than 10 ppm in good yield and efficiency.

In a specific example where 1 kg of Sample 2 having a TOTAL-RE of 94.7% by weight is employed, pure water is weighed and added to bring 1 kg of the Sample to a volume of 14.3 liters.

In the next step of forming oxalates, the following reaction is utilized.

$$2RECl_3 + 3H_2C_2O_4 \rightarrow RE_2(C_2O_4)_3 + 6HCl$$

In this case, 3 mols of $H_2C_2O_4$ is theoretically required for 2 mols of $RECl_3$ according to the reaction formula. However, according to the process of the present invention, good results are obtainable when $H_2C_2O_4$ is added in an amount of from 0.3 to 1.8 times, preferably from 0.5 to 1.5 times, the theoretical amount. If the amount is outside this range, the efficiency for the recovery of rare earth components decreases, and the concentrations of the Fe and Ca impurities are likely to exceed 5 ppm and 10 ppm, respectively, such being undesirable. Specifically, for instance, relative to 14.3 liters of the solution, 27.8 liters of a solution containing 0.5 mol/liter of high grade oxalic acid is weighed and added. At the time of the addition, it is necessary that the solution is heated and stirred at a temperature of at least 70° C., preferably at least 80° C. If the temperature is lower than 70° C., it is likely that the removal of Fe, Zn and Ca can not adequately be carried out. After the completion of the addition of oxalic acid, if the stirring is continued for further 15 to 20 minutes, the reaction for the precipitation of rare earth oxalates can more adequately be ensured.

Thereafter, the reaction system is left to stand still, whereby the precipitation reaction is completed and a clear supernatant is obtained. Then, a step of washing the oxalates is conducted. The washing is conducted with warm pure water at a temperature of at least 50° C., preferably at least 80° C. in an amount of at least 15000 times the volume of the precipitate slurry. This is a particularly important condition in the present invention to avoid adsorption of Fe or other impurities ions.

Some examples illustrating the effects of the precipitation temperature in the above-mentioned step for forming oxalates and the effects of the washing temperature in the above-mentioned step for washing the oxalates, are given in Table 2. These data were obtained by using, as the waste rare earth phosphor, Sample 1 containing great amounts of Fe and Ca as presented in Table 1.

TABLE 2

| Temperature for the precipitation of oxalates | Temperature of washing water | Fe (ppm) | Ca (ppm) | Zn (ppm) |
|---|---|---|---|---|
| 15° C. | 15° C. | 14.9 | 63.3 | 305 |
| | 50° C. | 7.4 | 61.2 | |
| | 80° C. | 6.9 | 60.6 | 122 |
| 50° C. | 15° C. | 7.7 | 21.1 | |
| | 50° C. | 3.1 | 16.0 | 52.4 |
| | 80° C. | 2.2 | 14.3 | 41.1 |
| 80° C. | 15° C. | 1.2 | 10.7 | |
| | 50° C. | 0.5 | 8.4 | 4.8 |
| | 80° C. | 0.5 | 1.0 | 1.8 |

After the washing, water is removed under reduced pressure by means of e.g. a Nutsche funnel.

Then, the precipitates obtained are placed in a crucible and baked in air at a temperature of e.g. 1000° C. for 1 hour in a conventional manner, whereby a rare earth oxide such as $Y_2O_3$ is obtained. The rare earth oxide thereby obtained is extremely pure with $Ca < 10$ ppm and $Fe < 5$ ppm. Further, for instance, the $Y_2O_3$ thereby obtained may be used as a starting material and adjusted for the Eu, Tb and Sm concentrations to obtain a $Y_2O_2S:Eu$ phosphor in a conventional manner, and if necessary, red iron oxide is coated thereon, to obtain properties necessary for CPT or CDT, such as luminance and grain size. It is possible to obtain the phosphor properties which are adequate for practical use.

Needless to say, the process of the present invention is applicable not only to the $Y_2O_2S:Eu$ waste phosphor but also other rare earth oxysulfide waste phosphors such as waste phosphors composed mainly of $La_2O_2S$ or $Gd_2O_2S$.

Further, the process of the present invention is likewise applicable to waste phosphors other than the above oxysulfide waste phosphors, such as waste phosphors based on rare earth oxides which include $Y_2O_3$, $La_2O_3$ and $Gd_2O_3$.

Furthermore, according to the experiments conducted by the present inventors, it has been confirmed that in the case where the waste rare earth phosphor does not contain Ca and Zn compounds, even when the TOTAL-RE is 40% by weight, it is possible to bring the Fe content to less than 5 ppm by the application of the above operation, and thus the process of the present invention is useful also in such a case.

Now, the present invention will be described in further detail with reference to Examples. However, it should be understood that the present invention is by no means restricted to these specific Examples.

EXAMPLE 1

Into a porcelain evaporating dish (effective volume: 5000 ml), 350 g of the waste phosphor of Sample 1 as identified in Table 1 was put, and 2450 g of pure water and 956 g of a concentrated hydrochloric acid solution (specific gravity: 1.180) were added thereto. Then, 621 g of a hydrogen peroxide solution (specific gravity: 1.1327) was added thereto. After the completion of the reaction, the residue was filtered off. After the entire amount was filtered, pure water was added to the filtrate to bring the total volume to 5000 ml. The total 5000 ml of this solution was placed in a 20 liter beaker. The solution was heated to 80° C., and 9.22 liters of an oxalic acid solution (0.5 mol/liter) was added thereto. After the formation of the oxalates, the oxalates were precipitated and the supernatant was removed. The concentrated oxalates thereby obtained were about 2 liters. Hot pure water was added thereto to bring the total volume to 10 liters, and then oxalates were washed by high speed agitation. During this washing operation, the temperature of the solution was kept at a level of at least 80° C. The stirring time was 20 minutes. The washing operation was repeated 6 times. After the washing, the system was left to stand still, whereby the oxalates precipitated. The precipitates were subjected to water removal by means of a Nutsche funnel, whereby rare earth oxalates were obtained. The oxalates were transferred to a quartz crucible and baked at 1000° C. for 1 hour. The rare earth oxides thereby obtained, had a Fe content of 1.1 ppm and a Ca content of 2.1 ppm.

EXAMPLE 2

Into a porcelain evaporating dish (effective volume: 5000 ml), 350 g of the waste phosphor of Sample 2 as identified in Table 1 was put, and 2450 g of pure water and 1170 g of a concentrated hydrochloric acid solution (specific gravity: 1.180) were added thereto. Then, 262 g of a hydrogen peroxide solution (specific gravity: 1.1327) was added thereto. After the completion of the reaction, the residue was filtered off. After the entire amount was filtered, pure water was added to the filtrate to bring the total volume to 5000 ml. The total 5000 ml of this solution was placed in a 20 liter beaker. The solution was heated to 80° C., and 9.72 liters of an oxalic acid solution (0.5 mol/liter) was added thereto. After the formation of the oxalates, the oxalates were precipitated and the supernatant was removed. The concentrated oxalates thereby obtained were about 2 liters. Hot pure water was added thereto to bring the total volume to 10 liters, and then oxalates were washed by high speed agitation. During this washing operation, the temperature of the solution was kept at a level of at least 80° C. The stirring time was 20 minutes. The washing operation was repeated 6 times. After the washing, the system was left to stand still, whereby the oxalates precipitated. The precipitates were subjected to water removal by means of a Nutsche funnel, whereby rare earth oxalates were obtained. The oxalates were transferred to a quartz crucible and baked at 1000° C. for 1 hour. The rare earth oxides thereby obtained, had a Fe content of 0.7 ppm and a Ca content of 1.4 ppm.

EXAMPLE 3

Into a porcelain evaporating dish (effective volume: 5000 ml), 350 g of the waste phosphor of Sample 3 as identified in Table 1 was put, and 2800 g of pure water and 1100 g of a concentrated hydrochloric acid solution (specific gravity: 1.180) were added thereto. Then, 400 g of a hydrogen peroxide solution (specific gravity: 1.1327) was added thereto. After the completion of the reaction, the residue was filtered off. After the entire amount was filtered, pure water was added to the filtrate to bring the total volume to 5000 ml. The total 5000 ml of this solution was placed in a 20 liter beaker. The solution was heated to 80° C., and 9.88 liters of an oxalic acid solution (0.5 mol/liter) was added thereto. After the formation of the oxalates, the oxalates were precipitated and the supernatant was removed. The concentrated oxalates thereby obtained were about 2 liters. Hot pure water was added thereto to bring the total volume to 10 liters, and then oxalates were washed by high speed agitation. During this washing operation, the temperature of the solution was kept at a level of at least 80° C. The stirring time was 20 minutes. The washing operation was repeated 6 times. After the washing, the system was left to stand still, whereby the oxalates precipitated. The precipitates were subjected to water removal by means of a Nutsche funnel, whereby rare earth oxalates were obtained. The oxalates were transferred to a quartz crucible and baked at 1000° C. for 1 hour. The rare earth oxides thereby obtained, had a Fe content of 0.2 ppm and a Ca content of 0.2 ppm.

EXAMPLE 4

Into a quartz vat, 500 g (inclusive of water) of the waste phosphor of Sample 4 as identified in Table 1 was put, and it was baked in an electric furnace at 500° C. for 1 hour. After cooling, the baked sample was roughly pulverized and sieved to remove aluminum foils and other foreign matters and to obtain a waste phosphor powder. Into a porcelain evaporating dish (effective volume: 5000 ml), 350 g of the waste phosphor powder was put, and 2800 g of pure water and 1170 g of a concentrated hydrochloric acid solution (specific gravity: 1.180) were added thereto. Then, 262 g of a hydrogen peroxide solution (specific gravity: 1.1327) was added thereto. After the completion of the reaction, the residue was filtered off. After the entire amount was filtered, pure water was added to the filtrate to bring the total volume to 5000 ml. The total 5000 ml of this solution was placed in a 20 liter beaker. The solution was heated to 80° C., and 9.72 liters of an oxalic acid solution (0.5 mol/liter) was added thereto. After the formation of the oxalates, the oxalates were precipitated and the supernatant was removed. The concentrated oxalates thereby obtained were about 2 liters. Hot pure water was added thereto to bring the total volume to 10 liters, and then oxalates were washed by high speed agitation. During this washing operation, the temperature of the solution was kept at a level of at least 80° C. The stirring time was 20 minutes. The washing operation was repeated 6 times. After the washing, the system was left to stand still, whereby the oxalates precipitated. The precipitates were subjected to water removal by means of a Nutsche funnel, whereby rare earth oxalates were obtained. The oxalates were transferred to a quartz crucible and baked at 1000° C. for 1 hour. The rare earth oxides thereby obtained, had a Fe content of 3.2 ppm and a Ca content of 0.1 ppm.

Further, when water at room temperature was used for washing the oxalates, the Fe content in the obtained rare earth oxides was 9.5 ppm.

EXAMPLE 5

Into a porcelain evaporating dish (effective volume: 5000 ml), 350 g of the waste phosphor of Sample 5 as identified in Table 1 was put, and 2800 g of pure water and 1050 g of a concentrated hydrochloric acid solution (specific gravity: 1.180) were added thereto. Then, 588 g of a hydrogen peroxide solution (specific gravity: 1.1327) was added thereto. After the completion of the reaction, the residue was filtered off. After the entire amount was filtered, pure water was added to the filtrate to bring the total volume to 5000 ml. The total 5000 ml of this solution was placed in a 20 liter beaker. The solution was heated to 80° C., and 8.72 liters of an oxalic acid solution (0.5 mol/liter) was added thereto. After the formation of the oxalates, the oxalates were precipitated and the supernatant was removed. The concentrated oxalates thereby obtained were about 2 liters. Hot pure water was added thereto to bring the total volume to 10 liters, and then oxalates were washed by high speed agitation. During this washing operation, the temperature of the solution was kept at a level of at least 80° C. The stirring time was 20 minutes. The washing operation was repeated 6 times. After the washing, the system was left to stand still, whereby the oxalates precipitated. The precipitates were subjected to water removal by means of a Nutsche funnel, whereby rare earth oxalates were obtained. The oxalates were transferred to a quartz crucible and baked at 1000° C. for 1 hour. The rare earth oxides thereby obtained, had a Fe content of 3.1 ppm and a Ca content of 2.0 ppm.

Further, when water at room temperature was used for washing the oxalates, the Fe content in the obtained rare earth oxides was 8.0 ppm, and the Ca content was 10 ppm.

EXAMPLE 6

Into a porcelain evaporating dish (effective volume: 5000 ml), 350 g of the same waste phosphor as used in Example 2 (i.e. Sample 2 in Table 1) was put, and 2800 g of pure water and 1940 g of a concentrated nitric acid solution (specific gravity: 1.420) were added thereto. The solution was heated to facilitate the reaction. During the heating, the water level was carefully watched and adjusted by adding pure water. After the completion of the reaction, the system was left to cool, and the residue was filtered off. After the filtration of the entire amount, pure water was added to the filtrate to bring the total volume to 5000 ml.

Thereafter, in the same manner as in Example 2, oxalates were obtained, and then rare earth oxides were obtained. The rare earth oxides thereby obtained, had a Fe content of 0.2 ppm and a Ca content of 0.2 ppm.

EXAMPLE 7

Into a porcelain evaporating dish (effective volume: 5000 ml), 350 g of the same waste phosphor as used in Example 5 (i.e. Sample 5 in Table 1) was put, and 2800 g of pure water and 1745 g of a concentrated nitric acid solution (specific gravity: 1.420) were added thereto. The solution was heated to facilitate the reaction. During the heating, the water level was carefully watched and adjusted by adding pure water. After the completion of the reaction, the system was left to cool, and the residue was filtered off. After the filtration of the entire amount, pure water was added to the filtrate to bring the total volume to 5000 ml.

Thereafter, in the same manner as in Example 5, oxalates were obtained, and then rare earth oxides were obtained. The rare earth oxides thereby obtained, had a Fe content of 0.2 ppm and a Ca content of 1.0 ppm.

As described in the foregoing, according to the process of the present invention, it is possible to reuse expensive rare earth components as starting material for phosphors for CPT or CDT, with no substantial loss of the expensive rare earth components. Further, the removal of impurities can be carried out in a single step, and the recovery process step can thereby be simplified.

Furthermore, in the case where the waste rare earth phosphor contains an extremely large amount of impurities, it is possible to apply the treating step of the process of the present invention repeatedly to bring the impurity content to a sufficiently low level before application of the process of the present invention. Thus, the present invention is very useful for practical application.

What is claimed is:

1. A process for recovering highly pure rare earth oxides from a waste rare earth oxysulfide phosphor containing at least 500 ppm of Fe and/or 10 ppm of Ca impurities, which comprises:
   (a) dissolving the waste rare earth oxysulfide phosphor in an excess amount of a combination of hydrochloric acid and hydrogen peroxide;
   (b) adding oxalic acid to said solution at a temperature of at least 70° C. in an amount of from 0.3 to 1.8 times the theoretical amount, thereby precipitating rare earth oxalates from the solution; and
   (c) washing the precipitated rare earth oxalates with warm water having a temperature of at least 50° C., and baking the washed oxalates.

2. The process according to claim 1, wherein the waste rare earth oxysulfide phosphor is mainly composed of $Y_2O_2S$ phosphor.

3. The process according to claim 1, wherein the waste rare earth oxysulfide phosphor is mainly composed of $La_2O_2S$ phosphor.

4. The process according to claim 1, wherein the waste rare earth oxysulfide phosphor is mainly composed of $Gd_2O_2S$ phosphor.

5. The process according to claim 1, wherein the total amount of all rare earth oxysulfide compounds contained in the waste rare earth phosphor is at least 80% by weight as computed as $RE_2O_2S$.

6. The process according to claim 1, wherein the amount of hydrochloric acid is from 1.2 to 1.7 times the theoretically required amount of 6 mole and the amount of $H_2O_2$ is from 2 to 7 times the theoretically required amount of 1 mole.

7. The process according to claim 1, wherein the amount of oxalic acid present in solution ranges from 0.5 to 1.5 times the theoretical amount required for oxalate formation.

8. The process according to claim 1, wherein the temperature of the wash water of step (d) is at least 80° C.

9. The process according to claim 1, wherein said solution containing the dissolved phosphor is adjusted to a rare earth metal ion concentration of $0.5\pm0.1$ gram ion per liter in said solution.

10. The process according to claim 1, wherein said waste rare earth oxysulfide phosphor has a total rare earth metal compound content of at least 80% by weight, a Fe impurity content of at least 1,500 ppm and a Ca impurity content of at least 50.0 ppm.

* * * * *